United States Patent [19]

Rieu et al.

[11] Patent Number: 5,308,844
[45] Date of Patent: May 3, 1994

[54] SUBSTITUTED 3-PIPERAZINYLALKYL-2,3-DIHYDRO-4H-1,3-BENZOXAZIN-4-ONES AND THEIR USE IN THERAPY

[75] Inventors: Jean-Pierre Rieu; Dennis Bigg, both of Castres, France

[73] Assignee: Pierre Fabre Medicament, Boulogne, France

[21] Appl. No.: 925,493

[22] Filed: Aug. 5, 1992

[30] Foreign Application Priority Data

Aug. 5, 1991 [FR] France .................. 91 09946

[51] Int. Cl.⁵ .................. A61K 31/535; C07D 295/10
[52] U.S. Cl. .................. 514/230.5; 544/92
[58] Field of Search .................. 544/92; 514/230.5

[56] References Cited

U.S. PATENT DOCUMENTS

| 4,341,778 | 7/1982 | Mentrup | 514/230.5 |
| 4,789,675 | 12/1988 | Meguro et al. | 514/229.8 |
| 5,071,850 | 12/1991 | Rieu | 514/229.8 |

FOREIGN PATENT DOCUMENTS 359627 3/1990 European Pat. Off.

OTHER PUBLICATIONS

Chemical Abstracts 104(13) 10969s (1986).
Chemical Abstracts 71(17) 81384 (1969).
Chemical Abstracts 70 (19) 87821 (1969).

*Primary Examiner*—Mukund J. Shah
*Assistant Examiner*—Matthew V. Grumbling
*Attorney, Agent, or Firm*—Dressler, Goldsmith, Shore & Milnamow, Ltd.

[57] ABSTRACT

The invention relates to novel substituted 3-piperazinylalkyl-2,3-dihydro-4H-1,3-benzoxazin-4-ones of formula I

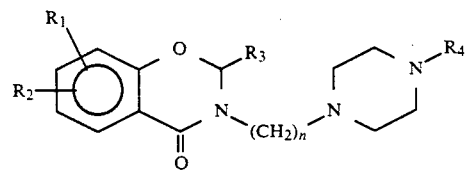

their pharmaceutically acceptable inorganic or organic salts, optionally in their hydrated form, the racemates, the enantismers or their mixtures, their preparation and their use as medicaments as well as all the pharmaceutical compositions of I which are or are not combined with another active principle.

11 Claims, No Drawings

SUBSTITUTED 3-PIPERAZINYLALKYL-2,3-DIHYDRO-4H-1,3-BENZOXAZIN-4-ONES AND THEIR USE IN THERAPY

The present invention made at the PIERRE FABRE Research Centre relates to novel substituted 3-piperazinylalkyl-2,3-dihydro-4H-1,3-benzoxazin-4-ones, their preparation process and their use as medicaments useful principally in cardiovascular disorders and disorders of the nervous system.

In a previous study, we have shown that derivatives of 3-alkylamino-4H-1,3-benzoxazin-4-ones have excellent properties in cardiovascular therapy and especially in the treatment of tachycardia, of cardiac rhythm disorder and of ischemia (EP Patent 359,627). During structural modifications at the level of the amine function, we noticed that the substitution of a phenylalkylamine by an arylpiperazine (compounds of the present invention) led to derivatives which had virtually lost their bradycardic activity but which on the other hand showed a powerful affinity for 5HT receptors and more precisely for $5HT_1A$.

Recent developments of the concept in the study of 5HT as a neuromediator and of its receptors have led to very dynamic research into compounds having a potential affinity for these receptors which is expressed by an action either at the cardiac level, or on the central nervous system. The discovery of a large number of compounds has justified the publication of recent developments in their pharmacological properties and the role of serotonin in the mode of action (cf. R. A. Glennon: Central Serotonin Receptors as Targets for Drug Research, J. Med. Chem. 30 (1) 1-12 (1987); P. R. Saxena and C. M. Villalon: Cardiovascular Effects of Serotonin Agonists and Antagonists, J. Cardiov. Pharmacol. 16 (suppl.7) S17-S34 (1990); I. Van Vijngaarden, M.Th.M. Tulp and W. Soudijn: The Concept of Selectivity in 5HT Receptor Research, Eur. J. Pharmacol. —Molecular Pharmacol. Section 188, 301-312 (1990); S. J. Peroutka: Receptor Families for 5HT, J. Cardiov. Pharmacol. 16 (suppl.3) S8-S14 (1990); J. R. Fozard: 5HT, The Enigma Variations, T.I.P.S. 8 (12) 501-506 (1987) etc . . . ).

Contrary to cyclic imides of the compounds previously described and containing a piperazinylalkyl group (cf. H. Wilkström and K. Svensson, Annual Reports in Medicinal Chemistry vol. 25, 41-50, Academic Press Inc (1989)), the compounds of the present invention which are derivatives of 3-piperazinylalkyl-4H-1,3-benzoxazin-4-ones of original structure have a single carbonyl function in the ring and a powerful affinity for 5-hydroxytryptamine receptors, of which the selectivity is a function of the substituents. Thus, these compounds can be used in disorders of the central nervous system as anxiolytics, antidepressants or antimigraine agents as well as in cardiovascular therapy as antihypertensives.

MOLECULES CLAIMED

The present invention more particularly relates to 3-piperazinylalkyl-4H-1,3-benzoxazin-4-ones of structure I

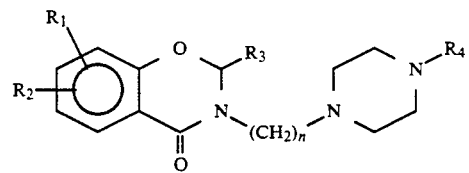

in which:

$R_1$ and $R_2$, which are identical or different, represent a hydrogen, a halogen, an alkyl group containing 1 to 6C, an alkyloxy group containing 1 to 4C, a hydroxyl, a nitro group, an amino which is unsubstituted or substituted by an acyl group or one or two alkyls each independently containing 1 to 4C; a sulfonylamino group; a halogen $R_3$ represents a hydrogen or an aliphatic group which is branched or unbranched and saturated or unsaturated, containing 1 to 5C;

$R_4$ represents either:

a phenyl group which is unsubstituted or substituted by one or more identical or different radicals, such as a halogen atom, an alkyl group containing 1 to 6C, an alkyloxy group containing 1 to 6C, a trifluoromethyl, a nitro group, an amino radical which is unsubstituted or substituted by one or more lower alkyl, acyl or carboxylate groups, all three containing 1 to 4 carbon atoms, a hydroxy group or a sulfonylamino group a monocyclic heteroaryl group containing one or two nitrogen atoms;

n can assume the values 2 to 6.

The present invention also includes the therapeutically acceptable inorganic or organic salts of the compounds of formula I, optionally in hydrated form. When the compounds of general formula I contain an asymmetric carbon, the present invention relates to the racemates as well as the various enantiomers, or their mixtures. The radicals $R_1$ and $R_2$ are preferentially chosen from amongst the following: H, $CH_3$, $CH_3CH_2$, $(CH_3)_2CH$, $CH_3O$, $CH_3CH_2O$, Br, Cl, F, OH, $NO_2$, $CH_3CONH$, $CH_3SO_2NH$, $(CH_3)_2N$. The radical $R_3$ is similarly preferentially represented by: H, $CH_3$, $CH_3CH_2$, $(CH_3)_2CH$, $CH_3—CH=CH$. The radical $R_4$ is more particularly represented by a group chosen from amongst:

a phenyl which can be unsubstituted or substituted by one or more of the following radicals: Br, Cl, F, $CF_3$, $CH_3$, $CH_3CH_2$, $CH_3O$, $CH_3CH_2O$, $NO_2$, OH, $NH_2$, $CH_3CONH$, $CH_3SO_2NH$, $(CH_3)_2N$, a pyridyl group, a pyrimidinyl group.

The present invention also relates to the use of the compounds of general formula I as a medicament and to the pharmaceutical compositions containing them. The pharmaceutical compositions according to the present invention can use one or more compounds of formula I, optionally combined with one or more other active principles. Finally, the processes for synthesis of the compounds of general formula I are also part of the present invention.

PROCESS OF PREPARATION OF THE COMPOUNDS OF FORMULA I

The best method of preparation of the derivatives of the general formula I consists in condensing a suitably substituted compound of formula II with a piperazine of formula III according to the scheme:

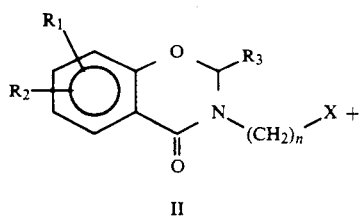

II

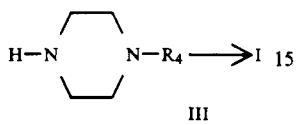

III where $R_1$ to $R_4$ and n have the same meaning as in general formula I and where X represents a halogen (Cl, Br, I) or else an alkanesulfonate group, preferentially the mesylate ($MeSO_3$) or an arylsulfonate group, especially the tosylate (p-$MeC_6H_4SO_3$). The condensation is preferably carried out at a temperature between 20° and 110° C. using or not using an excess of amine III and in the presence or absence of a base, similarly preferentially chosen from amongst pyridine or a tertiary amine, for example, triethylamine.

The products of the above reaction can be salified with the desired acid in an a polar or polar solvent such as ethyl acetate or ethanol as an example to give the expected monosalts or di-salts and their possible hydrates.

The following examples illustrate the invention without, however, limiting its scope.

EXAMPLE 1

Monohydrochloric
3-dihydro-3-[4-(4-(3-trifluoromethylphenyl)-piperazinyl)butyl]-4H-1,3-benzoxazin-4-one A mixture of 2.84 g (9.4 mmol) of 2,3-dihydro-3-(4-methanesulfonyloxybutyl)-4H-1,3-benzoxazin-4-one and of 3.27 g (14.2 mmol) of 4-(3-trifluoromethylphenyl)-piperazine in 1.32 ml (0.96 g or 9.4 mmol) of triethylamine is heated at 60° C. for 1 h 15. After returning to 25°, the mixture is poured into 80 ml of water and the pH is brought to 4.5 by addition of concentrated hydrochloric acid. The expected derivative is extracted with 2×50 ml of ethyl acetate and the organic solution is washed with water acidified to pH 4.5 and then with saturated brine and dried over sodium sulfate. After evaporation to dryness, the residue (m=3.55 g) is taken up in ethyl acetate, cooled in an ice bath and then treated to pH 2 with a solution of hydrochloric acid in ethyl acetate. The crystals formed are filtered, drained and rinsed with isopropyl ether. m=2.76 g (Yld=72%) of white powder of formula 1:

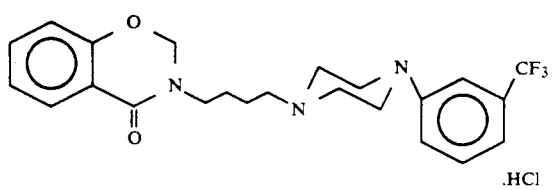

empirical formula: $C_{23}H_{27}ClF_3N_3O_2$ molecular weight: 469.935
powdery white crystals
melting point: 156° C.
IR (KBr) $\sqrt{}CO$ amide: 1675 $cm^{-1}$
NMR ($CDCl_3$) δ: 1.69–2.15 (m,4H); 2.85–3.2 (m,4H); 3.55–3.90 (m,8H); 5.21 (s,2H); 6.85–7.26 (m,5H); 7.30–7.6 (m,2H); 7.92 (dd,1H); 12.76 (s,1H); p.p.m.
soluble up to 6% in DMSO.

EXAMPLE 2

Monohydrochloride of
2,3-dihydro-3-[3-(4-phenylpiperazinyl)propyl]-4H-1,3-benzoxazin-4-one A mixture of 4.91 g (17.2 mmol) of 2,3-dihydro-3-(,3-methanesulfonyloxypropyl)-4H-1,3-benzoxazin-4-one and of 8.37 g (51.6 mmol) of 4-phenylpiperazine contained in a rotary evaporator with bulbs is heated at 50° C. for 30 min and the amine is then distilled at 50° C. under $10^{-3}$ mbar. The solid residue is taken up in 40 ml of water and 50 ml of toluene and the pH, is brought to 4 by addition of HCl, the phases are separated and extraction with toluene to pH 4 is repeated 3 times. The organic phases are reunited and the total phase is then washed with brine, dried over sodium sulfate and evaporated to dryness. The residual base (m=4.8 g) is taken up in a mixture of 40 ml of AcOEt and 10 ml of isopropyl alcohol, and after cooling to 0° C., a solution of hydrochloric acid in ethyl acetate is added to pH 2. The precipitate formed is filtered, drained and dried in an oven at 50° (m=4.5 g). The crystals are recrystallized twice in a mixture of AcOEt/iPrOH 40:60 to give 3.6 g (Yld54%) of white crystals of formula 2:

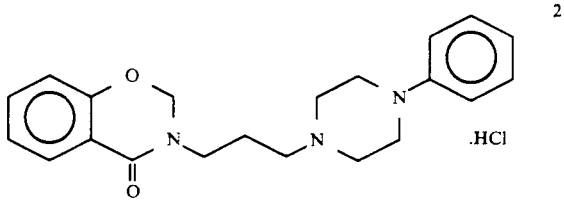

empirical formula: $C_{21}H_{26}ClN_3O_2$
molecular weight: 387.911
broken white crystals
melting point: 190° C.
IR (KBr) $\sqrt{}CO$ amide: 1670 $cm^{-1}$
NMR ($CDCl_3$) δ: 2.20–2.43 (m,2H); 2.9–3.2 (m,4H); 3.4–3.8 (m,8H); 5.28 (s,2H); 6.8–7.50 (m,7H); 7.88 (d,1H); 12.76 (s,1H); p.p.m.
soluble up to 1% in water.

EXAMPLE 3

Dihydrochloride of
2,3-dihydro-3-[2-(4-phenylpiperazinyl)ethyl]-4H-1,3-benzoxazin-4-one Using the working method described in Example 2 but starting from 2,3-dihydro-3-(2-methanesulfonyloxyethyl)-4H-1,3-benzoxazin-4-one, the compound 3 of formula:

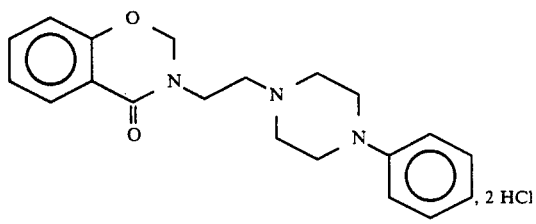

is obtained with a yield of 48%.
  empirical formula: $C_{20}H_{25}Cl_2N_3O_2$
  molecular weight: 410.345
  white crystals
  melting point: 206°–208° C.
  IR (KBr) $\sqrt{}$CO amide: 1666 cm$^{-1}$
  NMR (DMSO d$_6$)δ:3.1–3.50 (m, 6H) 3.6–4.0 (m, 6H); 5.47 (s,2H); 6.88 (t,1H); 6.95–7.4 (m,6H); 7.54 (t,1H); 7.81 (d,1H); 11.48 (s,1H); 12.32 (s,1H) p.p.m.
  soluble in water up to 1%.

EXAMPLE 4

Hydrochloride of 2.3-dihydro-3-[4-(4-phenylpiperazinyl)butyl]-4H-1,3-benzoxazin-4-one This compound is prepared according to the procedure described in Example 2 but starting from 2,3-dihydro-3-(4-methanesulfonyloxybutyl)-4H-1,3-benzoxazin-4-one with a yield of 65% and of formula 4:

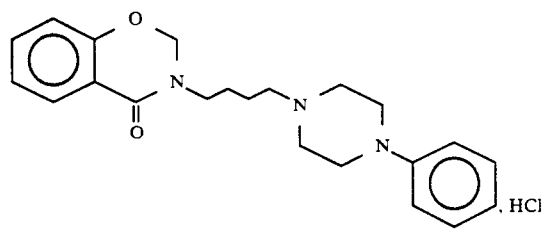

empirical formula: $C_{22}H_{28}ClN_3O_2$
molecular weight: 401.938
white crystals
melting point: 218°–220° C.
IR (KBr) $\sqrt{}$CO amide: 1670 cm$^{-1}$
NMR (CDCl$_3$) δ: 1.45–1.67 (m,2H); 1.68–1.90 (m,2H); 2.7–3.5 (m,12H); 5.02 (s,2H); 6.6–6.8 (m,4H); 6.9 (t,1H); 7.07 (t,2H); 7.15–7.28 (M,1H); 7.68 (dd,1H); 12.14 (s,1H) p.p.m.
soluble in water up to 0.5%.

EXAMPLE 5

Dihydrochloride of 2,3-dihydro-3-[2-(4-(2-methoxyphenyl)piperazinyl)ethyl]-4H-1,3-benzoxazin-4-one According to the procedure described in Example 1 but starting from 1-(2-methoxyphenyl)piperazine and 2,3-dihydro-3-(2-methanesulfonyloxyethyl)-4H-1,3-benzoxazin-4-one, compound 5 is obtained after recrystallization from isopropyl alcohol with a yield of 58% and of formula:

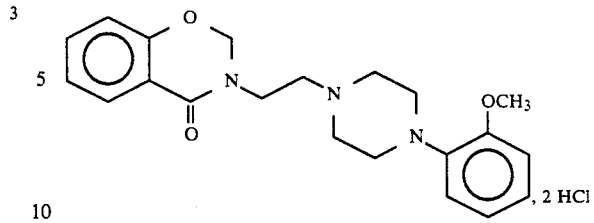

empirical formula: $C_{21}H_{27}Cl_2N_3O_3$
molecular weight: 440.451
white crystals
melting point: 206° C.
IR (KBr) $\sqrt{}$CO amide: 1655 cm$^{-1}$
NMR (base) (CDCl$_3$) δ: 2.5–2.8 (m,6H); 2.9–3.2 (m,4H); 3.75 (t,2H); 3.86 (s,3H); 5.31 (s,2H); 6.7–7.20 (m,6H); 7.3–7.6 (m,1H); 7.97 (dd,1H); p.p.m
soluble in water up to 6%.
The monohydrochloride was also isolated.
  empirical formula: $C_{21}H_{26}ClN_3O_3$
  molecular weight: 403.91
  white crystals
  slow decomposition point: 206°–207° C.
  soluble in water up to 0.9%.

EXAMPLE 6

Hydrochloride of 2,3-dihydro-3-[3-(4-(2-methoxyphenyl)piperazinyl)-propyl]-4H-1,3-benzoxazin-4-one The use of the process described in Example 1 with (2-methoxyphenyl)piperazine leads, with a yield of 42%, to compound 6- having as formula:

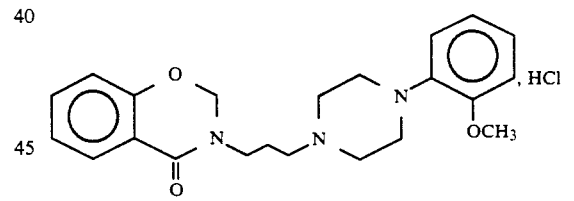

empirical formula: $C_{22}H_{28}ClN_3O_3$
molecular weight: 417.937
white powder
slow melting point: 190° C.
IR (KBr) $\sqrt{}$CO amide: 1660 cm$^{-1}$
NMR (CDCl$_3$) δ: 2.2–2.5 (m,2H); 2.8–3.5 (m,4H); 3.6–4 (m,11H); 5.3 (s,2H); 6.8–7.2 (m,6H); 7.3–7.6 (m,1H); 7.9 (dd,1H); 12.6 (s,1H); p.p.m.
soluble in water up to 0.5%.

EXAMPLE 7

Monohydrate of the dihydrochloride of 2,3-dihydro-3-[4-(4-(2-methoxyphenyl)piperazinyl)-butyl]-4H-1,3-benzoxazin-4-one Adapting the procedure of Example 1 to (2-methoxyphenyl)piperazine and to 2,3-dihydro-3-(4-methanesulfonyloxybutyl)-4H-1,3-benzoxazin-4-one, the compound 7 of formula:

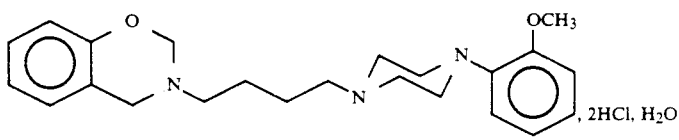

is obtained after recrystallization from isopropyl alcohol with a yield of 61%.

empirical formula: $C_{23}H_{33}Cl_2N_3O_4$
molecular weight: 486.44
broken white crystals
melting point: 202° C.
IR (KBr) $\sqrt{}$CO amide: 1665 cm$^{-1}$
NMR (CDCl$_3$) δ: 1.5–2.1 (m,4H); 2–3.2 (m,2H); 3.2–4.6 (m,6H); 3.95 (s,3H); 4–4.3 (m,2H); 4.85 (t,2H); 5.14 (s,2H); 6.2–7.6 (m,6H +H$_2$O); 7.81 (dd,1H); 8.00 (dd,1H) 13.12 (s,1H); p.p.m.
soluble in water up to 3%.

EXAMPLE 8

Monohydrochloride of 2,3-dihydro-3-[2-(4-(2-methylphenyl)piperazinyl)ethyl]-4H-1,3-benzoxazin-4-one Starting from (2-methylphenyl)piperazine and 2,3-dihydro-3-(2-methanesulfonyloxyethyl)-4H-1,3-benzoxazin-4-one, and working according to the working method described in Example 1, the compound 8 having as formula:

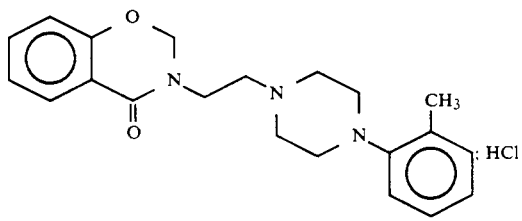

is obtained after recrystallization from methanol with a yield of 71%.

empirical formula: $C_{21}H_{26}ClN_3O_2$
molecular weight: 387.89
white prismatic crystals
melting point: 216° C.
IR (KBr) $\sqrt{}$CO amide: 1661 cm$^{-1}$
NMR (CDCl$_3$) δ: 2.27 (s,3H); 2.9–3.2 (m,4H); 3.25–3.85 (m,6H); 4.21 (t,3H); 5.45 (s,2H); 6.80–7.3 (m,6H); 7.35–8.6 (m,1H); 7.91 (dd,1H); 12.9 (s,1H); p.p.m.
soluble up to 0.35% in water.

EXAMPLE 9

Hydrochloride of 2.3-dihydro-3-[2-(4-(3-chlorophenyl)piperazinyl)ethyl]-4H-1,3-benzoxazin-4-one The use of the working method described in Example 1 with 3-chlorophenylpiperazine and 2,3-dihydro-3-(2-methanesulfonyloxyethyl)-4H-1,3-benzoxazin-4-one, allows the compound 9 of formula:

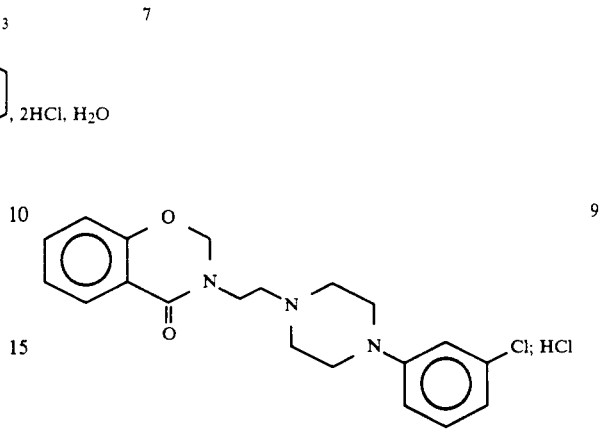

to be prepared after purification in methanol and with a yield of 59%.

empirical formula: $C_{20}H_{23}Cl_2N_3O_2$
molecular weight: 408.31
broken white crystals
melting point: 182° C.
IR (KBr) $\sqrt{}$CO amide: 1660 cm$^{-1}$
NMR (DMSO d$_6$) δ: 2.8–3.4 (m,4H); 3.5–3.8 (m,6H); 4.11 (t,3H); 5.4 (s,2H); 6.6–7 (m,4H); 7.05–7.20 (m,2H); 7.3–7.5 (m,1H); 7.84 (dd,1H); 12.1 (s,1H); p.p.m.
soluble in DMSO up to 10%.

EXAMPLE 10

Hydrochloride of 2,3-dihydro-3-[2-(4-(3-trifluoromethylphenyl)-piperazinyl)ethyl-4H-1,3-benzoxazin-4-one Starting from 3-trifluoromethylphenylpiperazine and 2,3-dihydro-3-(2-methanesulfonyloxyethyl)-4H-1,3-benzoxazin-4-one, and using the process of Example 1, the compound 10 of formula:

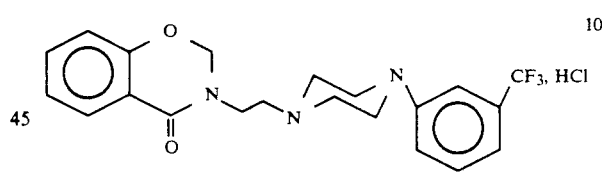

is obtained with a yield of 63%.

empirical formula: $C_{21}H_{23}ClF_3N_3O_2$
molecular weight: 441.88
white powdery crystals
melting point: 196° C.
IR (KBr) $\sqrt{}$CO amide: 1670 cm$^{-1}$
NMR (CDCl$_3$) δ: 2.9–3.2 (m,2H); 3.37 (t,2H); 3.5–3.9 (m,6H); 4.12 (t,2H); 5.39 (s,2H); 6.8–7.2 (m,5H); 7.25–7.5 (m,2H); 7.7 (dd,1H); 12.77 (s,1H); p.p.m.
soluble in DMSO up to 7%.

EXAMPLE 11

Hydrochloride of 2,3-dihydro-3-[2-(4-(2-pyridinyl)piperazinyl)ethyl]-4H-1,3-benzoxazin-4-one The use of the process of Example 1 adapted to 2-pyridinylpiperazine and 2,3-dihydro-3-(2-methanesulfonyloxyethyl)-4H-1,3-benzoxazin-4-one, leads, after recrystallization in methanol, to the compound 11 having as formula:

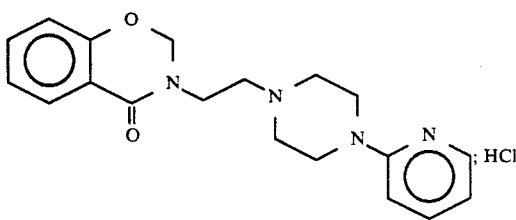

with a yield of 49%.
empirical formula: $C_{19}H_{23}ClN_4O_2$
molecular weight: 374.86
white needle-shaped crystals
melting point: 196° C.
IR (KBr) $\sqrt{}CO$ amide: 1661 cm$^{-1}$
NMR (DMSO d$_6$) δ: 2.5–4.9 (m,13H); 5.42 (s,2H); 8.5–7.8 (m,2H); 6.9 (d,1H); 7.12 (t,1H); 7.4–7.7 (m,2H); 7.91 (dd,1H); 8.19 (d,1H), p.p.m.
soluble in water up to 0.3%.

EXAMPLE 12

Hydrochloride of 2,3-dihydro-3-[2-(4-(2-pyrimidinyl)piperazinyl)ethyl]-4H-1,3-benzoxazin-4-one The use of the process described in Example 1 with 2-pyrimidylpiperazine condensed with 2,3-dihydro-3-(2-methanesulfonyloxyethyl)-4H-1,3-benzoxazin-4-one, allows the compound 12 of formula:

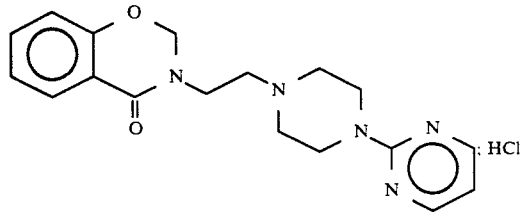

to be prepared with a yield of 39% after purification in a mixture of isopropanol/methanol.
empirical formula: $C_{18}H_{22}ClN_5O_2$
molecular weight: 375.86
white crystals
melting point: 234° C.
IR (KBr) $\sqrt{}CO$ amide: 1659 cm$^{-1}$
NMR (DMSO d$_6$) δ: 2.9–3.53 (m,6H); 3.68 (m,2H); 3.92 (m,2H); 4.69 (m,2H); 5.45 (s,2H); 6.77 (t,1H); 7.0–7.25 (m,2H); 7.55 (t,1H); 7.81 (d,1H); 8.45 (d,2H); 11.15 (s,1H); p.p.m.
soluble in water up to 1.2%.

EXAMPLE 13

Hydrochloride of 2.3-dihydro-6-methyl-3-[2-(4-(2-methoxyphenyl)-piperazinyl)ethyl]-4H-1,3-benzoxazin-4-one The adaptation of the process described in Example 1 to (2-methoxyphenyl)piperazine condensed with 6-methyl-2,3-dihydro-3-(2-methanesulfonyloxyethyl)-4H-1,3-benzoxazin-4-one gives, after recrystallization in isopropanol, the compound 13 of formula:

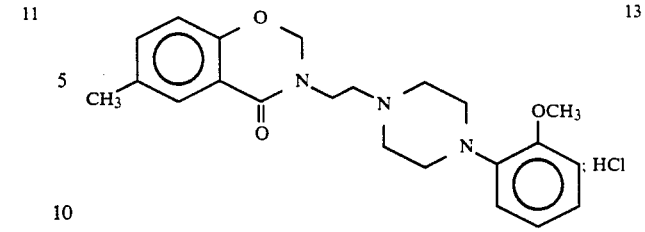

with a yield of 81%.
empirical formula: $C_{22}H_{28}ClN_3O_3$
molecular weight: 417.937
white crystals
melting point: 216° C.
IR (KBr) $\sqrt{}CO$ amide: 1667 cm$^{-1}$
NMR (DMSO d$_6$) δ: 2.33 (s,1H); 3.1–3.44 (m,4H); 3.52 (d,4H); 3.72 (d,2H); 3.86 (s,3H); 4.19 (t,2H); 5.41 (s,2H); 6.7–7.15 (m,5H); 7.27 (d,1H); 7.70 (s,1H); 12.84 (s,1H) p.p.m.
soluble in DMSO up to 3%.

EXAMPLE 14

Hydrochloride of 6-chloro-2.3-dihydro-3-[2-(4-(2-methoxyphenyl)-piperazinyl)ethyl]-4H-1,3-benzoxazin-4-one The condensation of 6-chloro-2,3-dihydro-3-(2-methanesulfonyloxyethyl)-4H-1,3-benzoxazin-4-one on to (2-methoxyphenyl)piperazine according to the process of Example 1 gives, after recrystallization in ethanol, the compound 14 having as formula:

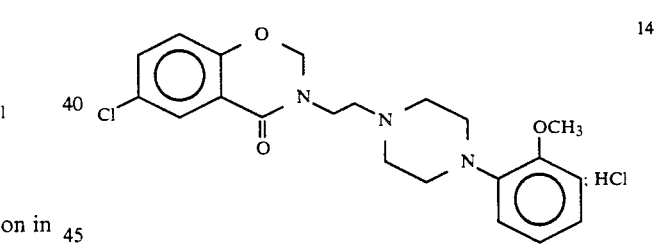

with a yield of 71%.
empirical formula: $C_{21}H_{25}Cl_2N_3O_3$
molecular weight: 438.355
white crystals
melting point: 228° C.
IR (KBr) $\sqrt{}CO$ amide: 1671 cm$^{-1}$
NMR (CDCl$_3$) δ: 3.1–3.42 (m,4H); 3.5 (d,4H); 3.72 (d,2H); 3.66 (s,3H); 4.20 (t,2H); 5.47 (s,2H); 6.8–7.2 (m,5H); 7.4 (dd,1H); 7.68 (d,1H); 12.83 (s.1H); p.p.m.
soluble in DMSO up to 1%.

EXAMPLE 15

Hydrochloride of 6-methoxy-2,3-dihydro-3-[2-(4-(2-methoxyphenyl)-piperazinyl)ethyl]-4H-1,3-benzoxazin-4-one By reaction of 2,3-dihydro-6-methoxy-3-(2-methanesulfonyloxyethyl)-4H-1,3-benzoxazin-4-one with (2-methoxyphenyl)piperazine according to the working method of Example 1, and after purification in isopropanol, the compound 15 of formula:

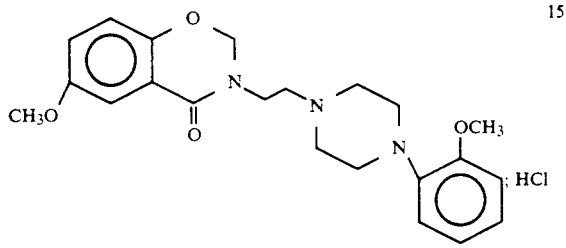

is prepared with a yield of 59%.
empirical formula: $C_{22}H_{28}ClN_3O_4$
molecular weight: 433.936
white crystals melting point: 242° C.
IR (KBr) $\sqrt{}$CO amide: 1666 cm$^{-1}$
NMR (CDCl$_3$) δ: 3.19 (m,2H); 3.35 (m,2H); 3.52 (m,4H); 3.6-3.9 (m,8H); 4.19 (t,2H); 5.4 (s,2H); 6.66-7.11 (m,6H); 7.36 (d,2H); 12.82 (s,1H); p.p.m.
soluble in DMSO up to 1.3%.

EXAMPLE 16

Hydrochloride of 2,6-dihydro-6-methoxy-3-[2-(4-(3-trifluoromethyl-phenyl)piperazinyl)ethyl]-4H-1,3-benzoxazin-4-one Adapting the working method of the previous example to (3-trifluoromethylphenyl)piperazine, compound 16 having as formula:

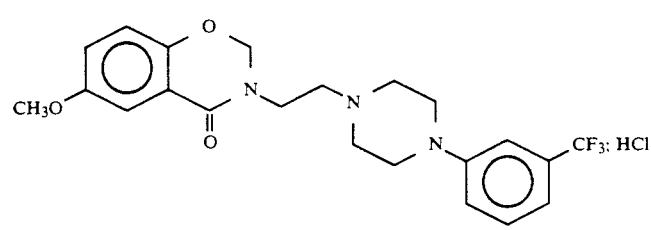

is prepared with a yield of 79%.
empirical formula: $C_{22}H_{25}ClF_3N_3O_3$
molecular weight: 471.907
powdery white crystals
melting point: 198° C.

IR (KBr) $\sqrt{}$CO amide: 1671 cm$^{-1}$
NMR (CDCl$_3$) δ: 3-3.3 (m,2H); 3.4-3.55 (m,2H); 3.6-4.05 (m,9H); 4.19 (t,2H); 6.92 (d,1H); 7.00-7.25 (m,4H); 7.3-7.5 (m,2H); 13.17 (s,1H); p.p.m.
soluble in DMSO up to 7%.

EXAMPLE 17

Hydrochloride of 2,3-dihydro-6,7-dimethoxy-3-[4-(4-(2-methoxyphenyl)-piperazinyl)butyl]-4H-1,3-benzoxazin-4-one When 2,3-dihydro-6,7-dimethoxy-3-(4-methanesulfonyloxybutyl)-4H-1,3-benzoxazin-4-one is condensed onto (2-methoxyphenyl)piperazine according to the process described in Example 1, compound 17 is prepared, after recrystallization in boiling methanol with a yield of 41% and of formula:

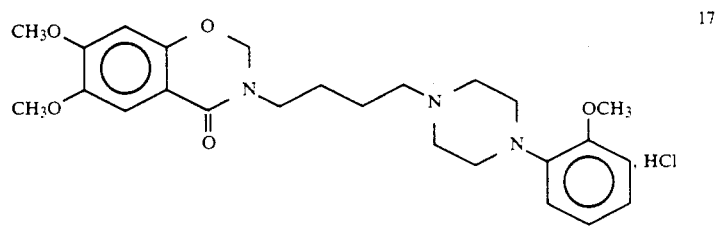

empirical formula: $C_{25}H_{34}ClN_3O_5$
molecular weight: 492.016
white prismatic crystals
melting point: 240° C.
IR (KBr) $\sqrt{}$CO amide: 1650 cm$^{-1}$
NMR (CDCl$_3$) δ: 1.6-1.9 (m,2H); 1.95-2.1 (m,2H); 2.9-3.3 (m,4H); 3.35-3.7 (m,8H); 3.8-4 (m,9H); 5.16 (s,2H); 8.46 (s,1H); 8.7-7.15 (m,4H); 7.32 (s,1H); 12.49 (s,1H); p.p.m.
soluble in water up to 0.2%.

EXAMPLE 18

Hydrochloride of 2,3-dihydro-6,7-dimethoxy-3-[4-(4-(3,4-dimethoxy-phenyl)piperazinyl)butyl]-4H-1,3-benzoxazin-4-one The use of the process described in the previous example, but using (3,4-dimethoxyphenyl)piperazine as starting material, leads, after purification in a methanol/ethanol mixture, to compound 18 with a yield of 83% and having as formula:

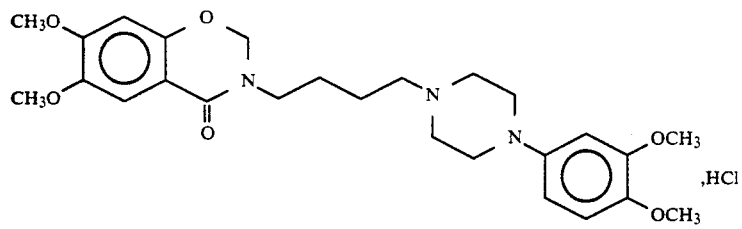

empirical formula: $C_{26}H_{36}ClN_3O_6$
molecular weight: 552.042
white crystals
melting point: 230° C.
IR (KBr) $\sqrt{}CO$ amide: 1656 cm$^{-1}$
NMR (CDCl$_3$) δ: 1.7–1.9 (m,2H); 1.9–2.2 (m,2H); 2.9–3.25 (m,4H); 3.3–3.8 (m,8H); 3.8–4.1 (m,12H); 5.17 (s,2H); 6.4–6.7 (m,3H); 6.77 (dd,1H); 7.31 (s,1H); 12.59 (s,1H); p.p.m.
soluble in DMSO up to 2%.

EXAMPLE 19

Hydrate of the (dl) hydrochloride of 2.3-dihydro-2-methyl-3-[2-(4-(3-trifluoromethyl-phenyl)piperazinyl)ethyl]-4H-1,3-benzoxazin-4-one Using the process described in EXAMPLE 1 but starting from 2,3-dihydro-2-methyl-3-(2-methanesulfonyloxyethyl)-4H-1,3-benzoxazin-4-one and 3-trifluoromethylphenylpiperazine as starting material, compound 19 having as formula:

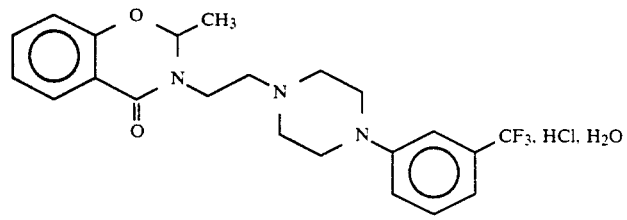

is obtained after purification in isopropyl alcohol with a yield of 74%.
empirical formula: $C_{22}H_{27}ClF_3N_3O_3$
molecular weight: 473.92
white crystals
melting point: 161° C.
IR (KBr) $\sqrt{}CO$ amide: 1670 cm$^{-1}$
NMR (CDCl$_3$) δ: 1.63 (d,3H); 2.08 (s,2H water); 3.41 (m,2H); 3.66 (m,6H); 4.02 (m,1H); 4.24 (m,1H); 5.77 (q,1H); 6.95 (d,1H); 7.19 (m,4H); 7.44 (dd,1H); 7.67 (dd,1H); 13.12 (s,1H); p.p.m.
soluble in DMSO up to 2%.

BIOLOGICAL EXPERIMENTS a) Pharmacological study: 5HT$_1$A binding

The 5HT$_1$A binding studies were carried out according to the technique of Peroutka (cf. Peroutka S. J., J. Neurochem. 47, p. 529–40, 1986). Male Charles River rats are stunned and decapitated, and the brain is removed and dissected. The different cerebral areas obtained are used or preserved at less than 20° C. The hippocampus is ground in a Polytrone ® (20 seconds at 7) in 20 volumes of 50 mM tris HCl buffer pH 7.7 at 25° C.) and centrifuged at 45000 g for 10 min. The pellet is separated, taken up in the same volume of tris buffer and incubated for 10 min at 37° C. and then recentrifuged for 10 min at 45000 g. The pellet is finally taken up in 100 volumes of tris HCl buffer containing 10 µM of pargyline, 4 mM of CaCl$_2$ and 0.1% of ascorbic acid. The mixture obtained is homogenized in a Dounce.

The binding is carried out starting with 0.8 ml of the above membrane suspension to which 0.1 ml of $^3$H-8-OH-DPAT ligand (at a concentration of 1 nM) and either 0.1 ml of tris buffer (control) or the compound of the above invention is added. After incubation for 30 min at 25° C., the mixture is filtered on GF/B (Whatman) and rinsed with 5 ml of cold tris HCl buffer. The residue and the filter are then introduced into a vial containing 3 ml of Instagel liquid scintillant (Packard) and the radioactivity is measured in a Packard counter (Tri-Carbs).

The IC$_{50}$ are determined graphically for a concentration of ligand of 1 nM.

Table I gives the IC$_{50}$ for the 5HT$_1$A receptors for certain derivatives of the invention by way of nonlimiting example.

| Compound from Example | IC$_{50}$ nM |
|---|---|
| 1 | 7 |
| 5 | 5 |
| 14 | 5 |
| 15 | 2.2 |

2) Therapeutic uses

Taking account of their pharmacological activity, the derivatives of the present invention can be used in human or animal therapy in disorders of the central nervous system or cardiovascular disorders.

On account of their action on the 5HT$_1$A receptor, the compounds of the present invention are more precisely indicated at the CNS level in the treatment of depressive states or of anxiety, optionally in sleep disorders and the regulation of food intake. Other compounds are more precisely useful at the cerebrovascular and cardiovascular level in the treatment of hypertension and optionally of migraine.

The compounds of the present invention are also used to prepare medicoments. Their administration can be carried out orally, parenterally or rectally; each dose is formed of an inert pharmaceutical adjuvant facilitating the preparation of the medicament and the absorption of the active principle which can be combined with another.

These medicaments can be in the form of tablets, gelatin capsules, suspensions, emulsions, syrups, suppositories, solutions or the like.

The administration of the active principle can be effected at a daily dose between 5 and 800 mg.

The following preparation is given as a nonlimiting example, and the ingredients as well as others can be introduced in other proportions without modifying the scope of the invention.

EXAMPLE 20 tablets

| | |
|---|---|
| Hydrochloride of 6-methoxy-2,3-dihydro-3-[2-(2-methoxy-4-phenylpiperazinyl)ethyl]-4H-1,3-benzoxazin-4-one | 25 mg |
| Lactose | 15 mg |
| Cornstarch | 50 mg |
| Magnesium stearate | 5 mg |
| Polyvinylpyrrolidone | 10 mg |
| Carboxymethylcellulose | 30 mg |

We claim:

1. A derivative of 2,3-dihydro-4-(piperazinylalkyl)-4H-1,3-benzoxazin-4-one of formula I

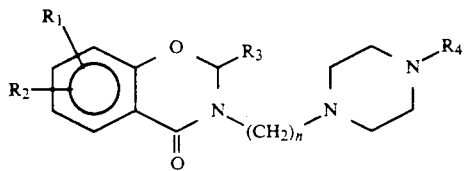

in which the substituents are defined as follows:

$R_1$ and $R_2$, which are identical or different, represent a hydrogen, a lower alkyl group containing 1 to 6 carbons, which is branched or unbranched; a lower alkyloxy group containing 1 to 4 carbons; a hydroxyl; a nitro; an amino which is unsubstituted or substituted by an acyl group or one or two alkyls, each independently containing 1 to 4 carbons; a sulfonylamino group; a halogen;

$R_3$ represents a hydrogen, an aliphatic group which is branched or unbranched and saturated or unsaturated, containing 1 to 5 carbons;

$R_4$ represents either:
  a phenyl group which can be unsubstituted or substituted by one or more identical or different radicals, chosen from amongst the following:
    a lower alkyl group containing 1 to 6 carbons, which is linear or branched,
    an alkyloxy group containing 1 to 6 carbons, which is linear or branched,
    a halogen,
    a trifluoromethyl,
    a nitro group,
    a hydroxy group,
    an amino which is unsubstituted or substituted by one or more alkyl groups, an acyl or a carboxylate, all three containing 1 to 4 carbons; a sulfonylamino group,
    a monocyclic heteroaryl group containing one or two nitrogen atoms selected from the class consisting of pyrridyl and pyrimidinyl groups;

n can assume the values 2 to 6; as well as the therapeutically acceptable inorganic or organic salts of I;

and also the racemates and the various enantiomers, or their mixtures when the compounds of the formula I contain an asymmetric carbon.

2. A compound as claimed in claim 1, wherein the radicals $R_1$ and $R_2$ are chosen from the group consisting of: H, $CH_3$, $CH_3CH_2$, $(CH_3)_2CH$, $CH_3O$, $CH_3CH_2O$, Br, Cl, F, OH, $NO_2$, $NH_2$, $CH_3CONH$, $CH_3SO_2NH$, and $(CH_3)_2N$.

3. A compound as claimed in one of claims 1 or 2, wherein the radical $R_3$ is represented by a member of the group consisting of: H, $CH_3$, $CH_3CH_2$, $(CH_3)_2CH$, and $CH_3-CH=CH$.

4. A compound as claimed in one of claims 1 or 2, wherein the radical $R_4$ is represented either by:
  a phenyl which can be unsubstituted or substituted by one or more of the following radicals: Br, Cl, F, $CF_3$, $CH_3$, $CH_3CH_2$, $CH_3O$, $CH_3CH_2O$, $NO_2$, OH, $NH_2$, $CH_3CONH$, $CH_3SO_2NH$, $(CH_3)_2N$,
  a pyridyl group,
  a pyrimidinyl group.

5. A compound of general formula I as claimed in one of claims 1 or 2, which is chosen from amongst:
Hydrochloride of 2,3-dihydro-3-[4-(4-(3-trifluoromethylphenyl)piperazinyl)butyl]-4H-1,3-benzoxazin-4-one
Hydrochloride of 2,3-dihydro-3-[3-(4-phenylpiperazinyl)propyl]-4H-1,3-benzoxazin-4-one
Dihydrochloride of 2,3-dihydro-3-[2-(4-phenylpiperazinyl)ethyl]-4H-1,3-benzoxazin-4-one
Hydrochloride of 2,3-dihydro-3-[4-(4-phenylpiperazinyl)butyl]-4H-1,3-benzoxazin-4-one
Dihydrochloride of 2,3-dihydro-3-[2-(4-(2-methoxyphenyl)piperazinyl)ethyl]-4H-1,3-benzoxazin-4-one
Hydrochloride of 2,3-dihydro-3-[3-(4-(2-methoxyphenyl)piperazinyl)propyl]-4H-1,3-benzoxazin-4-one
Hydrate of the dihydrochloride of 2,3-dihydro-3-[4-(4-(2-methoxyphenyl)piperazinyl)butyl]-4H-1,3-benzoxazin-4-one
Hydrochloride of 2,3-dihydro-3-[2-(4-(2-methylphenyl)piperazinyl)ethyl]-4H-1,3-benzoxazin-4-one
Hydrochloride of 2,3-dihydro-3-[2-(4-(3-chlorophenyl)piperazinyl)ethyl]-4H-1,3-benzoxazin-4-one
Hydrochloride of 2,3-dihydro-3-[2-(4-(3-trifluoromethylphenyl)piperazinyl)ethyl]-4H-1,3-benzoxazin-4-one
Hydrochloride of 2,3-dihydro-3-[2-(4-(2-pyridinyl)piperazinyl)ethyl]-4H-1,3-benzoxazin-4-one
Hydrochloride of 2,3-dihydro-3-[2-(4-(2-pyrimidinyl)piperazinyl)ethyl]-4H-1,3-benzoxazin-4-one
Hydrochloride of 2,3-dihydro-6-methyl-3-[2-(4-(2-methoxyphenyl)piperazinyl)ethyl]-4H-1,3-benzoxazin-4-one
Hydrochloride of 6-chloro-2,3-dihydro-3-[2-(4-(2-methoxyphenyl)piperazinyl)ethyl]-4H-1,3-benzoxazin-4-one
Hydrochloride of 6-methoxy-2,3-dihydro-3-[2-(4-(2-methoxyphenyl)piperazinyl)ethyl]-4H-1,3-benzoxazin-4-one
Hydrochloride of 2,6-dihydro-6-methoxy-3-[2-(4-(3-trifluoromethylphenyl)piperazinyl)ethyl]-4H-1,3-benzoxazin-4-one
Hydrochloride of 2,3-dihydro-6,7-dimethoxy-3-[4-(4-(2-methoxyphenyl)piperazinyl)butyl]-4H-1,3-benzoxazin-4-one Hydrochloride of 2,3-dihydro-6,7-dimethoxy-3-[4-(4-(3,4-dimethoxyphenyl)piperazinyl)butyl]-4H-1,3-benzoxazin-4-one Hydrate of the (dl) hydrochloride of 2,3-dihydro-2-methyl-3-[2-(4-(3-trifluoromethylphenyl)piperazinyl)ethyl]-4H-1,3-benzoxazin-4-one 6. A pharmaceutical composition, which contains as active principle at least one compound as claimed in one of claims 1 or 2 combined with an inert pharmaceutical support.

7. A method of treating a patient suffering from depression which comprises administering to said patient a compound as defined in one of claims 1 or 2 in an amount effective as an anti-depressant.

8. A method of treating a patient suffering from anxiety which comprises administering to said patient a compound as defined in one of claims 1 or 2 in an amount effective as an anxiolytic agent.

9. A method of treating a patient suffering from migraine which comprises administering to said patient a compound as defined in one of claims 1 or 2 in an amount effective as an antimigraine agent.

10. A method of treating a patient suffering from hypertension which comprises administering to said patient a compound as defined in one of claims 1 or 2 in an amount effective as an antihypertensive agent.

11. A compound as claimed in claim 1 wherein said compound is a salt in hydrated form.

* * * * *

UNITED STATES PATENT AND TRADEMARK OFFICE
CERTIFICATE OF CORRECTION

PATENT NO. : 5,308,844
DATED : May 3, 1994
INVENTOR(S) : Rieu et al.

It is certified that error appears in the above-indentified patent and that said Letters Patent is hereby corrected as shown below:

In the Abstract, second paragraph, line 3, delete [enantismers] and insert -- enantiomers--.

In Column 7, Example 7, delete

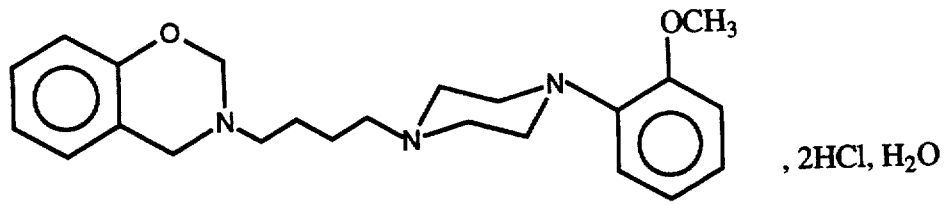

, 2HCl, H$_2$O and insert

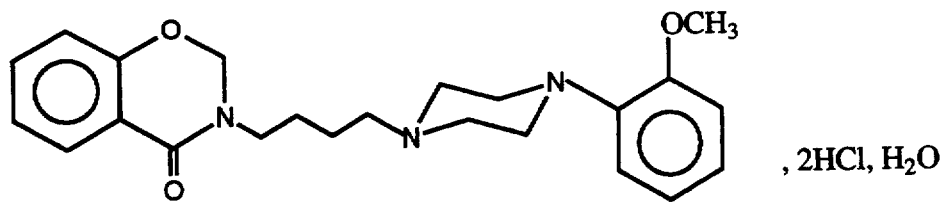

, 2HCl, H$_2$O

UNITED STATES PATENT AND TRADEMARK OFFICE
CERTIFICATE OF CORRECTION

PATENT NO. : 5,308,844

DATED : May 3, 1994

INVENTOR(S) : Rieu et al.

Page 2 of 3

It is certified that error appears in the above-indentified patent and that said Letters Patent is hereby corrected as shown below:

Column 2, line 43, after "$NO_2$," insert --$NH_2$,--.

Column 3, line 38, delete [Monohydrochloric] and insert --Monohydrochloride--.

Column 3, line 39, before "3-dihydro-..." insert --of 2,--.

Column 4, line 17, delete [2,3-dihydro-3-(,3] and insert --2,3-dihydro-3-(3--.

Column 4, line 23, after "pH" delete [,].

Column 4, line 37, delete [(Yld54%)] and insert Yld=54%--.

Column 4, line 55, delete [m,BH);] and insert --m,8H);--.

Column 5, line 19, after "(m,6H)" insert --;--.

Column 5, line 27, delete [2.3-dihydro-3] and insert 2,3-dihydro-3--.

Column 6, line 33, after "methoxyphenyl)" insert a hypen "-".

Column 6, line 37, delete [6-] and insert --6--.

Column 7, line 62, delete [2.3-dihydro] and insert --2,3-dihydro--.

Column 9, delete [2.3-dihydro] and insert --2,3-dihydro--.

Column 10, line 28, delete [2.3-dihydro] and insert --2,3-dihydro--.

Column 12, line 46, delete [2.3-dihydro] and insert --2,3-dihydro--.

Column 13, line 25, delete [2.3-dihydro] and insert --2,3-dihydro--.

UNITED STATES PATENT AND TRADEMARK OFFICE
CERTIFICATE OF CORRECTION

PATENT NO. : 5,308,844
DATED : May 3, 1994
INVENTOR(S) : Rieu et al.

It is certified that error appears in the above-indentified patent and that said Letters Patent is hereby corrected as shown below:

Column 13, line 50, delete [(s,2H water)] and insert --(s,2H:water)--.

Column 13, line 64, delete [Polytrone] and insert --Polytron--.

Column 14, line 67, delete [medicoments] and insert --medicaments--.

Column 16, line 36, delete [Dihydrochlorideof] and insert --Dihydrochloride of--.

Signed and Sealed this

Sixth Day of December, 1994

Attest:

BRUCE LEHMAN

Attesting Officer  Commissioner of Patents and Trademarks